United States Patent [19]

Daneshvar

[11] Patent Number: 5,263,966
[45] Date of Patent: Nov. 23, 1993

[54] DEVICE FOR SUPPRESSING POST-CATHETERIZATION WOUND BLEEDING

[76] Inventor: Yousef Daneshvar, 33200 Slocum, Farmington, Mich. 48024

[21] Appl. No.: 800,085

[22] Filed: Nov. 29, 1991

[51] Int. Cl.$^5$ ............................................. A61B 17/12
[52] U.S. Cl. ..................... 606/201; 606/202
[58] Field of Search ............ 606/202, 203, 201; 602/13; 128/96.1, 98.1, 686

[56] References Cited

U.S. PATENT DOCUMENTS

| | | | |
|---|---|---|---|
| 2,481,924 | 9/1949 | Hanafin | 606/202 |
| 3,171,410 | 3/1965 | Towle et al. | 606/201 X |
| 3,654,931 | 4/1972 | Hazlewood | 606/202 |
| 4,106,002 | 8/1978 | Hogue | 606/202 X |
| 4,175,562 | 11/1979 | Honan | 606/202 |
| 4,957,105 | 9/1990 | Kurth | 606/203 X |

FOREIGN PATENT DOCUMENTS 9011744 10/1990 PCT Int'l Appl. ............... 606/202

Primary Examiner—Michael H. Thaler

[57] ABSTRACT

After intervention of the vessels in the groin, a routine procedure is to apply pressure by a sand bag to prevent bleeding.

The device of the present invention is a better solution for this problem. It consists of a wrap which covers the groin area to support a specifically shaped pressure balloon when it is inflated. The balloon is inside a cover and the pressure inside it can easily be changed and monitored. A mesh inside a plastic tube may help to watch for bleeding. By using this wrap, a patient no longer need be motionless, and may even be allowed to stand if needed.

21 Claims, 5 Drawing Sheets

DEVICE FOR SUPPRESSING POST-CATHETERIZATION WOUND BLEEDING

FIELD OF THE INVENTION

This invention relates to the post-catheterization prevention of bleeding from a wound created as a consequence of inserting a catheter, or other similar device, into a vessel. More particularly, it relates to preventing bleeding from a wound proximate a person's groin.

BACKGROUND AND SUMMARY OF THE INVENTION

One of the common concerns in cardiac catheterization and related interventions is the problem of bleeding after catheterization of a vessel. This well known and familiar problem may even need corrective surgery in extreme cases.

A commonly used method of preventing such complication is quite primitive, and may be ineffective in some instances. That method is to position a sand bag in the area over a pressure bandage. In general, it may be considered a rather crude and uncomfortable method since, 1) it does not apply an appropriate amount of pressure all the time, 2) the sand bag may slide and/or fall, 3) the patient must be kept practically motionless to avoid dislocation of the sand bag, and 4) the patient is usually told not to raise the head over 15 degrees. Insofar as the applicant is aware, no other method has replaced the sand bag to any significant degree.

This problem has led to the applicant's creation of a much better alternative, which the applicant has named the D. Device. This device affords much easier use, gives much better pressure control, and is more comfortable for the patient. Not only can the patient move more, but it is believed that he/she may be discharged earlier from the hospital.

Briefly, the device is designed to prevent bleeding after catheterization of a groin vessel in connection with any of a number of different interventions, such as angiography for the heart, brain, arteries, etc., during which a vessel, such as an artery, has to be entered for diagnostic or treatment purposes. Naturally, the resulting wound has tendency to bleed.

The device comprises a main wrap, made preferably from tough synthetic fabric, which wraps around both the lower abdomen and the upper thighs to give support for the application of pressure to the groin by a specially shaped inflatable balloon contained within the wrap. The pressure inside the balloon can be monitored by a gauge, which can also have a safety alarm to indicate if the pressure inside the balloon drops. Another wrap, made preferably from a thin layer of non-irritating, soft, disposable material matching the shape of the main wrap may cover the skin under the main wrap to prevent contamination. Means are also provided so that bleeding which may occur after the device has been placed on the person can be seen by an observer. Further detail of the invention, and other features, will be seen as the description proceeds.

DESCRIPTION OF THE PREFERRED EMBODIMENT

Figure 1:
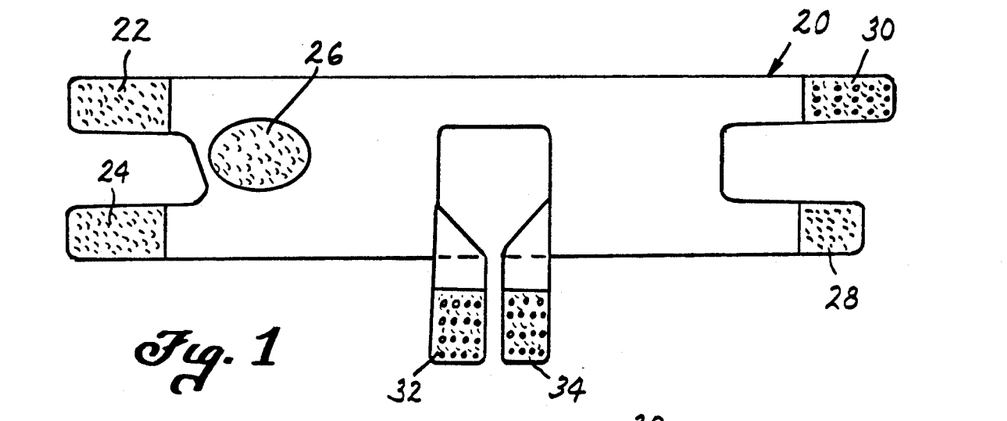
FIG. 1 is a front view of a wrap used in the invention.
Figure 2:
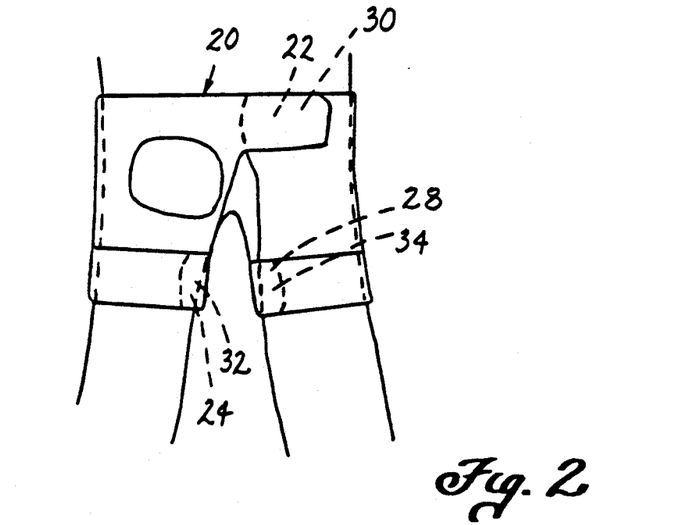
FIG. 2 is a front view showing the wrap in use on a person.

FIG. 1 shows the front view of a wrap 20 and its general appearance when opened and spread on a table. It has several areas containing Velcro TM. The soft parts 22, 24, 26, 28 of the Velcro TM are shown with straight lines, while the rough parts 30, 32, 34 are shown with dots. Parts 22, 24 are on the front face of wrap 20 as it appears in FIG. 1, and parts 30, 28 on the back face so that when wrap 20 is worn as shown in FIG. 2, the end containing soft part 22 will match and stick to part 30 to tighten the upper portion of the wrap around the lower abdomen, very much like a girdle or a belt. Part 24 will match with part 32 to wrap around the right upper thigh. Part 28 will match with part 34 to wrap around the left upper thigh. These will altogether hold the wrap tight in place.

Part 26 shown in FIG. 1 is a soft Velcro TM part and is disposed so that the back of a cover of a balloon, to be described next, will be in contact with, and stick to, it. The purpose of this part 26 is to allow adjustment of the position of the balloon and cover to the wrap in order to fit different patients. FIG. 2 gives a general idea of how wrap 20 will look when it is worn and in place on a patient's body.

Figure 3:
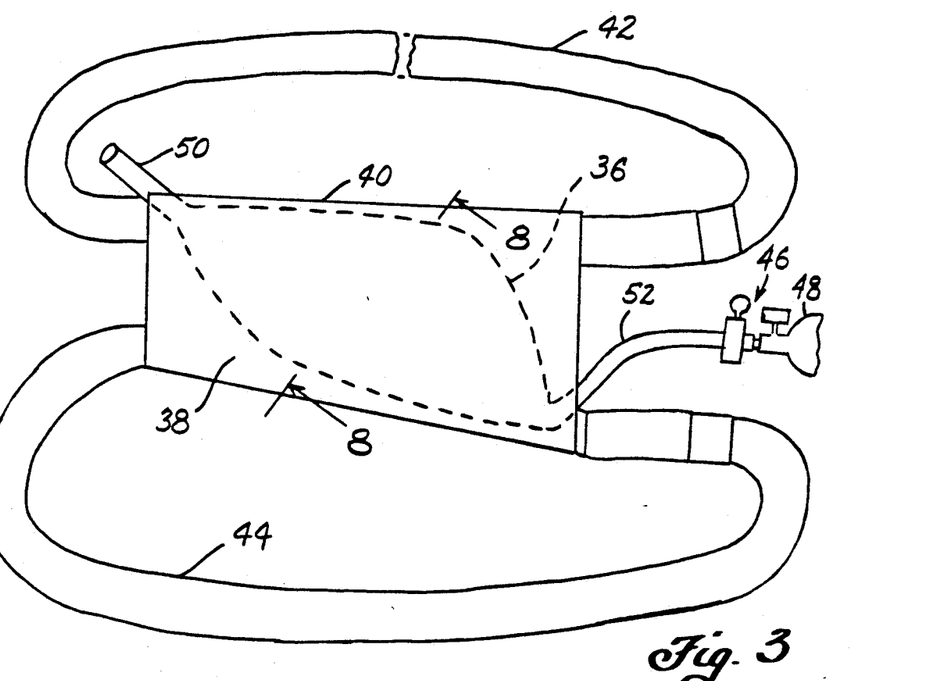
FIG. 3 is a front view of a balloon and cover used in the invention.
Figure 4:
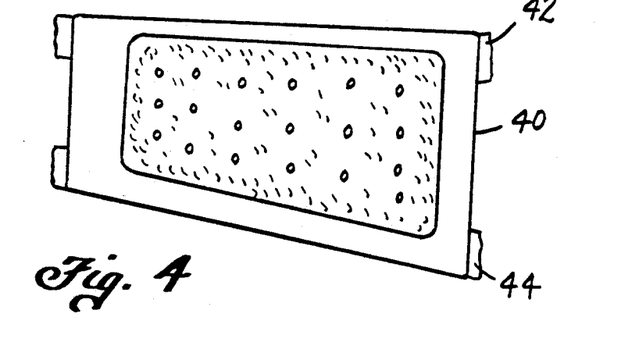
FIG. 4 is a fragmentary front view of the cover of FIG. 3 showing further detail.

FIG. 3 shows a balloon 36 inside a fabric pocket 38 of a cover 40 having straps 42, 44 extending from its corners and designed to wrap around the lower abdomen and the right thigh. The broken area in the upper strap 42 that goes around the abdomen is intended to show the disrupted piece. The lower strap 44 is to fit the upper part of the right thigh. The general appearance of balloon 36 is shown, along with its connection 46 to an inflating part 48 as well as a tube 50 to be connected to an alarm, to be described later.

Tube 50 is at one lengthwise end of balloon 36, and a further tube 52, leading to connection 46, is at the opposite lengthwise end. The two tubes 50, 52 protrude from pocket 38.

Figure 5:
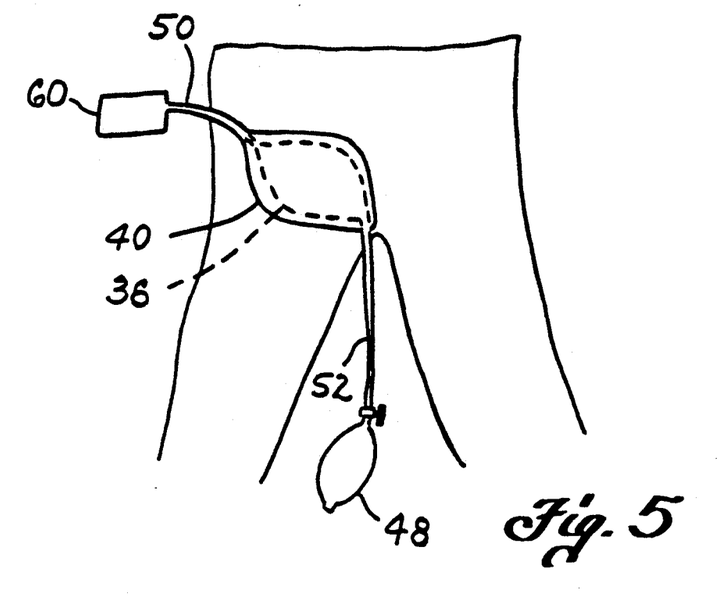
FIG. 5 is a front view showing the general application of the balloon and cover to the person's body, including an alarm associated with the balloon.
Figure 8:
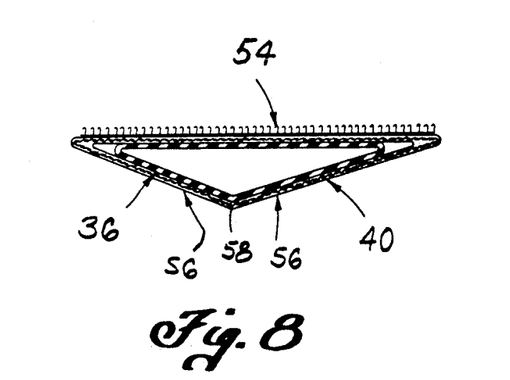
FIG. 8 is a traverse cross-sectional view in the direction of arrows 8—8 in FIG. 3.

In order to best fit and adapt to the shape and anatomy of the groin area and to mainly cover the area most liable for bleeding and hematoma, balloon 36 has an almost rhomboid shape, although it may have a different shape such as a circular or sausage-type shape, such different shapes not being shown in a drawing. As seen in FIGS. 3 and 5, balloon 36 tapers toward each lengthwise end so that it is noticeably wider in the middle than at its ends. As seen in FIG. 8, balloon 36 has a flat face 54 toward wrap 20, and an opposite angled face 56 toward the groin. Face 56 has a vertex that is to be situated in the groove of the groin line and that divides face 56 into an abdomen-confronting face portion and a thigh-confronting face portion.

Cover 40 is preferably a soft non-stretchable material to resist stretching. The cover of a regular blood pressure cuff is representative of such materials. Cover 40 has two faces: one to face the area of the groin, and the other containing a rough part 54 of Velcro TM to coincide and fit the matching part 26 on wrap 20 to hold the cover and balloon in place. Cover 40 can also be attached to wrap 20 by way of a couple of snaps. The balloon and its cover can be made from transparent plastic to allow observation of possible bleeding.

Wrap 20 is made from a durable, strong, but rather soft, fabric (similar to the synthetic fabric of many handbags and soft suitcases) designed to wrap around the lower abdomen and waist area with extensions to wrap around the upper parts of the thighs. This wrapping procedure can be achieved with the use of Velcro TM shown here and/or snaps and belt-like systems or the application of shoe tie types of techniques. The idea is to hold wrap 20 rather tightly in place to stand against pressure. When wrap 20 is held tight, then its strong non-stretchable fabric material will allow application of the force over the vessels and the adjacent areas where it is needed. The balloon's shape adapts to the shape of the groin area, and it should be strong enough to hold pressures of up to 250-300 mm of mercury.

Figure 6:
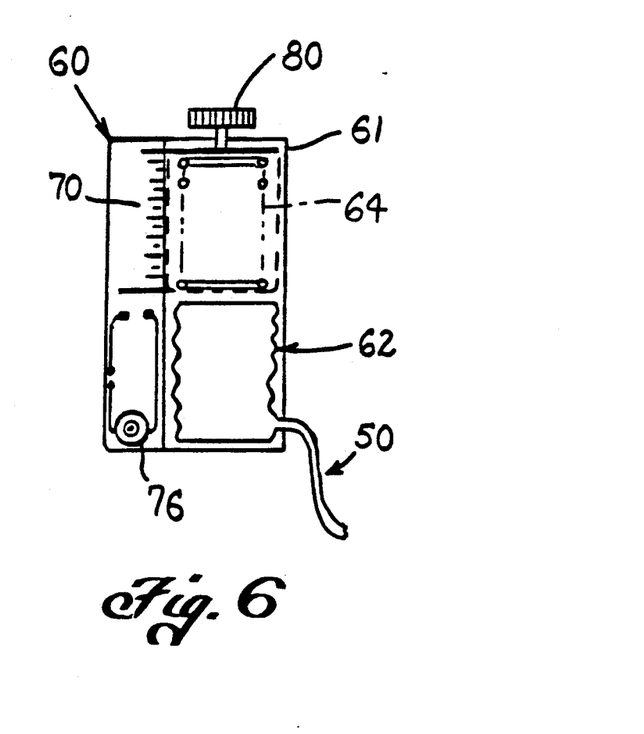
FIG. 6 is a front view of the alarm of FIG. 5 showing more detail.
Figure 6A:
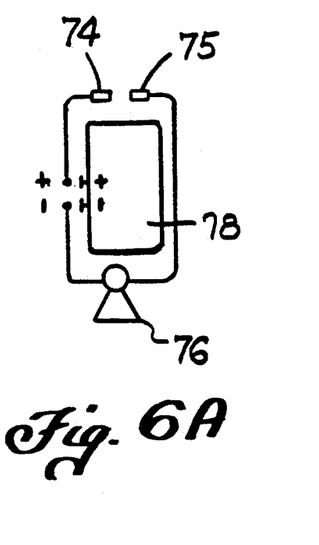
FIG. 6A is a fragmentary front view of a portion of the alarm of FIG. 6 showing better detail.
Figure 9:
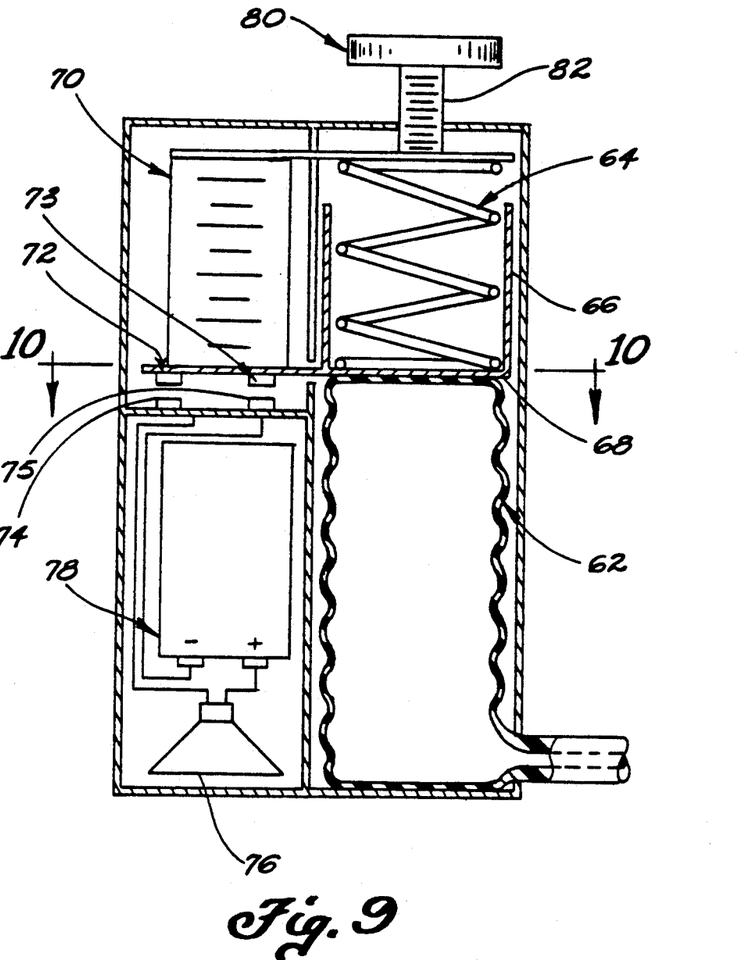
FIG. 9 is a more enlarged view of the alarm of FIG. 6.
Figure 10:
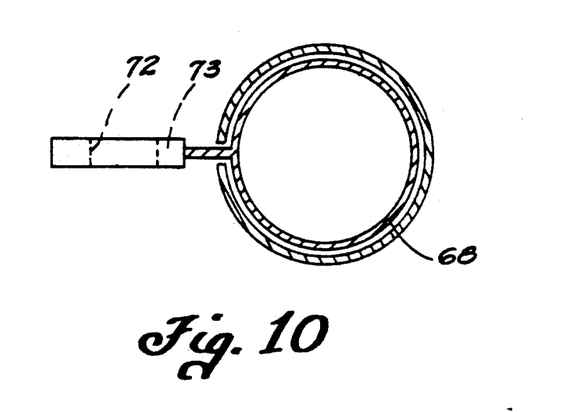
FIG. 10 is a transverse cross-sectional view in the direction of arrows 10—10 in FIG. 9.

With inflation of the balloon, the pressure will build up to be applied to the side of the vessel on the puncture side. This pressure can be monitored by connecting this part via tube 50 to the regular blood pressure monitor used in hospitals and offices or by a gauge designed for this job which is shown in FIGS. 6, 9, and 10, and which has a safety alarm part to indicate if the pressure drops. A small snap will allow the tube to be closed and the inflating device to be removed during transfers.

The alarm 60 comprises a small cylindrical box 61 having an accordion-type balloon 62 connected to balloon 36. This accordion balloon 62 will work against a circular coiled spring 64 inside box 61 and is separated by the flat, circular end plate of a cap 66 plate covering the lower end of spring 64. With a rise in the pressure inside balloon 36, this small accordion balloon 62 will be inflated, and distended and pressurized, and the pressure and distention will push cap 66 against spring 64.

Cap 66 is connected to a metal piece 68 which acts as a gauge. The gauge is to move against a scale 70 to show the relative amount of the pressure inside the balloon. If the pressure inside the balloon drops for any reason, i.e., perforation or leakage, spring 64 will push the metal piece 68 to connect its two metal terminals 72, 73 to terminals 74, 75 to complete an electric circuit and an electric buzzer 76 to sound. The circuit is powered by a battery 78. A control knob 80 comprising a screw 82 can be turned to position the top of spring 64 to adjust the level of pressure that will cause the alarm signal to sound. Turning control knob 80 also adjusts the pressure scale.

Figure 7:
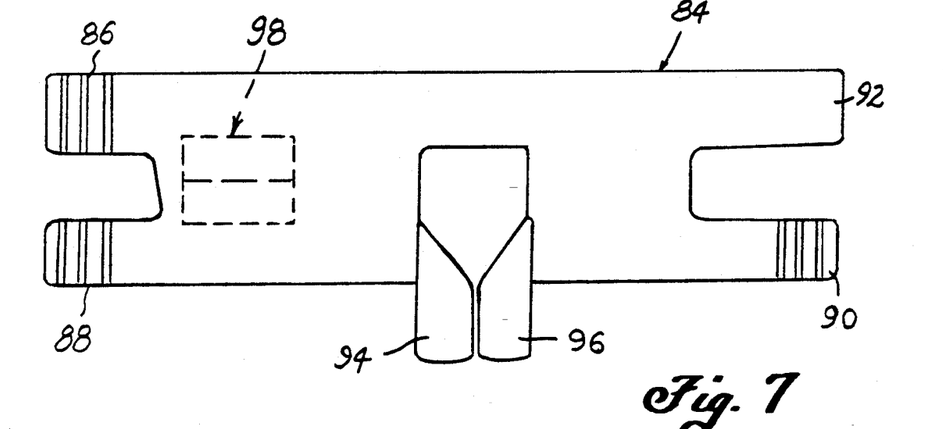
FIG. 7 is a front view of an inner wrap that may also be used in the invention.

FIG. 7 shows the front view of an inner wrap 84 and its general appearance when opened and spread on a table. It is very similar to wrap 20 mentioned earlier. It is designed to be used under the outside wrap 20 to prevent contamination of the skin and the spread of dirt and germs. Wrap 84 is a layer of thin, non-irritating, soft synthetic disposable material, with a cut very similar to the wrap 20 so as to fit inside it. In order to keep wrap 84 in place when used, it has lines of gluey or sticky areas that are covered and protected by a covering plastic or paper that will be removed to expose the gluey areas at the time of use. The gluey areas are 86, 88, and 90.

When wrap 84 is worn, area 86 will match and stick to the back part of an area 92 after the upper part of the wrap has been wrapped around the lower abdomen. Area 88 will match and stick to an area 94 after the lower right part of the wrap has been wrapped around the right upper thigh. Area 90 will match and stick to an area 96 after the lower right part of the wrap has been wrapped around the left upper thigh.

Wrap 84 has a rectangular area 98 to register with part 26 of main wrap 20. Area 98 can be cut open and folded to the upper and lower sides (or torn) to make a window through which part 54 can touch part 26 of wrap 20 to hold balloon 36 in place. If wrap 84 is used to cover the area under the balloon, then there will be no need to have this window opened.

Wrap 84 may consist of a sheet of plastic to prevent oozing of the blood or liquids outside of the wrap. It may be designed to attach inside of the outside wrap by way of snaps, gluey surfaces, or clips, etc., before its use. The sizes, relative shapes, color, and materials of wrap 20 may vary to match different people's size and body structure as well as the amount of the pressure needed for the job to be done. The shape of the balloon and its cover may be modified to fit the anatomy of the groin area in different people with different groin anatomy, and it could be wider or have a longer diagonal along the femoral artery to cover the lower part of the abdomen for the patients whose perforation of vessels is done over and above the groin areas.

Some parts of this wrap such as the cover for the left groin and the left thigh may be eliminated when the wrap is made to be used for right groin procedures, and vice versa. Further support can be achieved for higher pressure by adding hard plastic or metal sheets to the wall of the area over the groin to enable it to stand higher pressure. The shape of these sheets may be oval or quadrilateral with mild curvature in center to match the shape of the balloon. These hard sheets may be permanent parts of the structure of the wrap or inserted inside a pocket over the groin area in the wall of the wrap when needed.

In some models, the area over the wounded vessel can be made from transparent plastics to give the chance of watching for bleeding. In such cases, the Velcro TM part 54 will be removed from the area.

Figure 11:
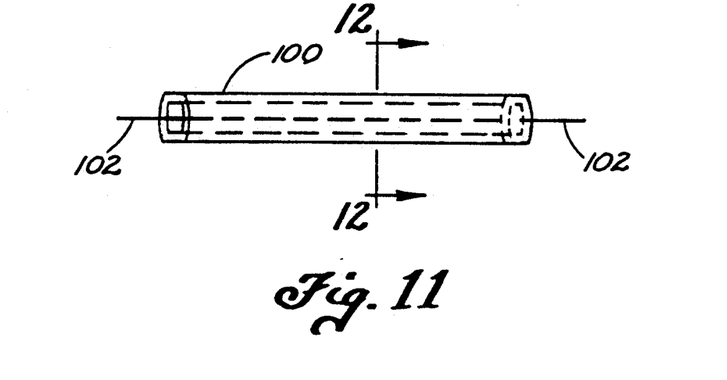
FIG. 11 is a top view of another part that may be used in the invention.
Figure 12:
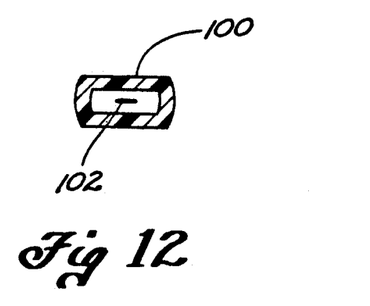
FIG. 12 is a transverse cross-sectional view in the direction of arrows 12—12 in FIG. 11.

FIGS. 11 and 12 show a clear transparent plastic tube 100 with 5 by 10 mm outside size and about 2 by 5 mm inside opening and 25 to 30 cm length, designed to resist pressure and to hold a hydrophilic cotton yarn or mesh 102 inside. One end of this mesh will be positioned directly over the wound area, and the tube will extend to other end to be exposed for observation outside of the wrap. This mesh is to absorb the blood if it oozed and carry along inside the tube to allow the blood to be noted and bleeding to be observed.

When properly placed in the area after a procedure, i.e., cardiac catheterization, the balloon will be over the artery which was intervened and then, after inflation, it will put the appropriate pressure desired in the area to prevent oozing of the blood. The pressure is easily controlled and it can be checked by a gauge. A mesh inside a plastic cover to be located under the balloon may help to notice bleeding, with absorption of the blood by the mesh and discoloration of its white color when contaminated with blood.

Further support when needed can be provided with the use of a hard piece of plastic or metal located over the balloon and inside a pocket in the wrap, or in the space between the wrap and the balloon.

The balloon 36 inside cover 40 may be enough to work in some cases alone without an outer wrap 20. A soft disposable cover may be made to cover this piece in order to prevent contamination.

In summary then, the disclosed balloon 36 and its cover 40 may be said to comprise a face 56 that confronts the person's groin line and portions of the person's abdomen and thigh on either side of the groin line. The vertex 58 fits into the groin, dividing this face 56 into an abdomen-confronting portion and a thigh-confronting portion. The balloon and cover have a length extending between tubes 50 and 52, a thickness that extends in the direction of pressure application to the underlying wound, and a width that is transverse to both the length and thickness.

What is claimed is:

1. A device for preventing bleeding from a wound created as a consequence of catherization of a vessel proximate a person's groin line, said device comprising a wrap having respective abdomen-wrap and thigh-wrap portions adapted for respective wrapping around a person's abdomen and thigh to respective sides of a person's groin line, inflatable balloon means adapted to be disposed between an underlying zone of a person and an overlying zone of said wrap that is adapted to overlie said underlying zone of a person, said underlying zone of a person comprising a person's groin line and portions of a person's abdomen and thigh proximate a person's groin line, means for inflating said balloon means to create pressure that is reacted by said wrap and consequently applied to said underlying zone of a person by a face of said balloon means that confronts said underlying zone of a person, said balloon means having a length that is adapted to extend along the length of a person's groin line, thickness that extends in the direction of pressure application by said balloon means to said underlying zone of a person, and width that is transverse to both the length and thickness of said face of said balloon means, said face of said balloon means comprising a lengthwise extending vertex that is adapted to fit into a person's groin line and divide said face of said balloon means into an abdomen-confronting face portion adapted for overlying a portion of a person's abdomen proximate a person's groin line and a thigh-confronting face portion adapted for overlying a portion of a person's thigh proximate a person's groin line.

2. A device as set forth in claim 1 in which said balloon means comprises another face that is opposite said first-mentioned face and confronts said wrap, and further including means for releasably securing said another face of said balloon means to said overlying zone of said wrap.

3. A device as set forth in claim 2 in which said balloon means comprises a cover enclosing a balloon and said means for releasably securing said another face of said balloon means to said overlying zone of said wrap is disposed between said cover and said overlying zone of said wrap.

4. A device as set forth in claim 1 in which said means for inflating said balloon means comprises a tube extending from said balloon means at one lengthwise end thereof.

5. A device as set forth in claim 4 in which said balloon means comprises a second tube extending from another lengthwise end of said balloon means opposite said first-mentioned lengthwise end thereof.

6. A device as set forth in claim 5 in which one of said tubes leads to an inflator for pressurizing said balloon means and the other of said tubes leads to a means for monitoring the inflation pressure of said balloon means.

7. A device as set forth in claim 1 further including a disposable inner wrap that separates said balloon means from said underlying zone of a person, said inner wrap having its own abdomen-wrap and thigh-wrap portions adapted for respective wrapping around a person's abdomen and thigh.

8. A device as set forth in claim 7 in which said inner wrap comprises an aperture between said balloon means and said first-mentioned wrap, and further including means for releasably securing said balloon means to said overlying zone of said first-mentioned wrap via said aperture.

9. A device as set forth in claim 7 in which said inner wrap comprises one or more adhesive zones that are covered by strippable release layers for exposing adhesive to secure the abdomen-wrap and thigh-wrap portions of said inner wrap onto said inner wrap after they have been wrapped around the person's abdomen and thigh.

10. A device as set forth in claim 1 further including a tube having a first portion thereof adapted to be disposed proximate the wound and a second portion extending from said first portion thereof so as to be visible, said second portion of said tube being transparent, and a hydrophilic material extending from the wound through said tube for conveying evidence of wound bleeding through said tube to said second portion of said tube so that such evidence can be visually observed.

11. A device as set forth in claim 1 in which said balloon means and said wrap comprise transparent material so that wound bleeding can be observed through them.

12. A device as set forth in claim 1 in which said balloon means has a general rhomboid shape so as to thus have greater width in the vicinity of the middle of its length than it has at its lengthwise ends.

13. A device as set forth in claim 1 in which said wrap is non-stretchable.

14. A device for preventing bleeding from a wound created as a consequence of catherization of a vessel proximate a person's groin line between a person's abdomen end thigh, said device comprising inflatable balloon means adapted for disposition over an underlying zone of a person which comprises a person's groin line and portions of a person's abdomen and thigh proximate a person's groin line, a wrap comprising an overlying zone for holding said balloon means against said underlying zone of a person, means for inflating said balloon means to create pressure that is reacted by said wrap and consequently applied to said underlying zone of a person, said balloon means having a length that extends along the length of a person's groin line, thickness that extends in the direction of pressure application by said balloon means to said underlying zone of a person, and width that is transverse to both the length and thickness of said balloon means, said means for inflating said balloon means comprising a tube that extends from one lengthwise end of said balloon means for an inflator for pressurizing said balloon means, and said balloon means comprising another tube extending from another lengthwise end of said balloon means opposite said first-mentioned lengthwise end to a means for monitoring the inflation pressure of said balloon means, in which said balloon means comprises a face that is adapted to confront said underlying zone of a person and has a lengthwise extending vertex that is adapted to fit into a person's groin line and divide said face into an abdomen-confronting face portion that is adapted to overlie a portion of a person's abdomen proximate a person's groin line and a thigh-confronting face portion that is adapted to overlie a portion of a person's thigh proximate a person's groin line.

15. A device as set forth in claim 14 in which said wrap comprises respective abdomen-wrap and thigh-wrap portions adapted for respective wrapping around a person's abdomen and thigh.

16. A device for preventing bleeding from a wound created as a consequence of catherization of a vessel proximate a person's groin line between a person's abdomen and thigh, said device comprising inflatable balloon means adapted for disposition over an underlying zone of a person which comprises a person's groin line and portions of a person's abdomen and thigh proximate a person's groin line, a wrap comprising an overlying zone for holding said balloon means against said underlying zone of a person, means for inflating said balloon means to create pressure that is reacted by said wrap and consequently applied to said underlying zone of a person, said balloon means having a length that extends along the length of a person's groin line, thickness that extends in the direction of pressure application by said balloon means to said underlying zone of a person, and width that is transverse to both the length and thickness of said balloon means, said means for inflating said balloon means comprising a tube that extends from one lengthwise end of said balloon means to an inflator for pressurizing said balloon means, and said balloon means comprising another tube extending from another lengthwise end of said balloon means opposite said first-mentioned lengthwise end to a means for monitoring the inflation pressure of said balloon means, in which said balloon means and said wrap comprise transparent material so that wound bleeding can be observed through them.

17. A device for preventing bleeding from a wound created as a consequence of catherization of a vessel proximate a person's groin line between a person's abdomen and thigh, said device comprising inflatable balloon means adapted for disposition over an underlying zone of a person which comprises a person's groin line and portions of a person's abdomen and thigh proximate a person's groin line, a wrap comprising an overlying zone for holding said balloon means against said underlying zone of a person, means for inflating said balloon means to create pressure that is reacted by said wrap and consequently applied to said underlying zone of a person, said balloon means having a length that extends along the length of a person's groin line, thickness that extends in the direction of pressure application by said balloon means to said underlying zone of a person, and width that is transverse to both the length and thickness of said balloon means, said means for inflating said balloon means comprising a tube that extends from one lengthwise end of said balloon means to an inflator for pressurizing said balloon means, and said balloon means comprising another tube extending from another lengthwise end of said balloon means opposite said first-mentioned lengthwise end to a means for monitoring the inflation pressure of said balloon means, in which said balloon means has a general rhomboid shape so as to have greater width in the vicinity of the middle of its length than it has at its lengthwise ends.

18. A device for preventing bleeding from a wound created as a consequence of catheterization of a vessel proximate a person's groin line between a person's abdomen and thigh, said device comprising inflatable balloon means adapted for disposition over an underlying zone of a person which comprises a person's groin line and portions of a person's abdomen and thigh proximate a person's groin line, a wrap comprising an overlying zone for holding said balloon means against said underlying zone of a person, means for inflating said balloon means to create pressure that is reacted by said wrap and consequently applied to said underlying zone of a person, said balloon means having a length that is adapted to extend along the length of a person's groin line, thickness that extends in the direction of pressure application by said balloon means to said underlying zone of a person, and width that is transverse to both the length and thickness of said balloon means, and indicator means providing for visible indication of wound bleeding, in which said indicator means comprises a tube having a first portion thereof adapted to be disposed proximate the wound and a second portion thereof extending from said first portion thereof so as to be visible, said second portion of said tube being transparent, and a hydrophilic material extending from the wound through said tube for conveying evidence of wound bleeding through said tube to said second portion of said tube so that such evidence can be visually observed.

19. A device for preventing bleeding from a wound created as a consequence of catheterization of a vessel proximate a person's groin line between a person's abdomen and thigh, said device comprising inflatable balloon means adapted for disposition over an underlying zone of a person which comprises a person's groin line and portions of a person's abdomen and thigh proximate a person's groin line, a wrap comprising an overlying zone for holding said balloon means against said underlying zone of a person, means for inflating said balloon means to create pressure that is reacted by said wrap and consequently applied to said underlying zone of a person, said balloon means having a length that is adapted to extend along the length of a person's groin line, thickness that extends in the direction of pressure application by said balloon means to said underlying zone of a person, and width that is transverse to both the length and thickness of said balloon means, and indicator means providing for visible indication of wound bleeding, in which said indicator means comprises said balloon means and said wrap comprising transparent material so that wound bleeding can be observed through them.

20. A device for preventing bleeding from a wound created as a consequence of catheterization of a vessel proximate a person's groin line, said device comprising a wrap having respective abdomen-wrap and thigh-wrap portions adapted for respective wrapping around a person's abdomen and thigh to respective sides of a person's groin line, inflatable balloon means adapted to be disposed between an underlying zone of a person and an overlying zone of said wrap that is adapted to overlie said underlying zone of a person, said underlying zone of a person comprising a person's groin line and portions of a person's abdomen and thigh proximate a person's groin line, means for inflating said balloon means to create pressure that is reacted by said wrap and consequently applied to said underlying zone of a person by a face of said balloon means that is adapted to confront said underlying zone of the person, said balloon means comprising its own abdomen-wrap and thigh-wrap portions that are additional to said abdomen-wrap and thigh-wrap portions of said wrap and that are for respective wrapping around a person's abdomen and thigh to respective sides of a person's groin line to hold said balloon means in place on a person preparatory to the wrapping of said abdomen-wrap and thigh-wrap portions of said wrap around a person's abdomen and thigh.

21. A device as set forth in claim 20, said balloon means having a length that is adapted to extend along the length of a person's groin line, thickness that extends in the direction of pressure application by said balloon means to said underlying zone of a person, and width that is transverse to both the length and thickness of said face of said balloon means, said face of said balloon means comprising a lengthwise extending vertex that is adapted to fit into a person's groin line and divides said face of said balloon means into an abdomen-confronting face portion adapted to overlie the portion of a person's abdomen proximate the person's groin lie and a thigh-confronting face portion adapted to overlie the portion of the person's thigh proximate the person'groin line.

* * * * *